United States Patent [19]
Pauling et al.

[11] Patent Number: 5,336,683
[45] Date of Patent: Aug. 9, 1994

[54] ANTIOXIDANTS

[75] Inventors: Horst Pauling, Bottmingen; Christof Wehrli, Witterswil, both of Switzerland

[73] Assignee: Hoffmann-La Roche Inc., Nutley, N.J.

[21] Appl. No.: 3,763

[22] Filed: Jan. 13, 1993

[30] Foreign Application Priority Data

Jan. 24, 1992 [CH] Switzerland ............................ 203/92
Nov. 25, 1992 [CH] Switzerland ........................ 3610/92

[51] Int. Cl.$^5$ ........................................ C07D 307/33
[52] U.S. Cl. ........................... 514/443; 514/444; 514/445; 549/33; 549/34
[58] Field of Search .................... 549/33, 34; 514/443, 514/444, 445

[56] References Cited
U.S. PATENT DOCUMENTS 5,116,999  5/1992  Le Roy et al. ..................... 549/34

OTHER PUBLICATIONS

The Van Nostrand Chemist's Dictionary, D. Van Nostrand Company, Inc., pp. 44 and 417 (New York 1953).

*Primary Examiner*—C. Warren Ivy
*Assistant Examiner*—Raymond Covington
*Attorney, Agent, or Firm*—George M. Gould; George W. Johnston; Alan P. Kass

[57] ABSTRACT

The invention is concerned with novel antioxidants, namely the [R] and, respectively, [S] compounds of the formula wherein $R^1$ and $R^2$ together represent the —S(O)— group and $R^3$ and $R^4$ represent hydrogen, or $R^3$ and $R^4$ together represent the —S(O)— group and $R^1$ and $R^2$ represent hydrogen.

9 Claims, No Drawings

ANTIOXIDANTS

The invention is concerned with novel antioxidants, namely the [R] and, respectively, [S] compounds of the formula

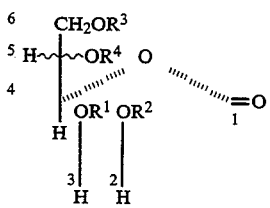

wherein $R^1$ and $R^2$ together represent the —S(O)— group and $R^3$ and $R^4$ represent hydrogen, or $R^3$ and $R^4$ together represent the —S(O)— group and $R^1$ and $R^2$ represent hydrogen, which are indicated by the wavy lines in formula I.

Also included are the epimers, racemates, diastereomers, and stereoisomers of the compounds of formula I.

Preferred compounds of formula I include in particular:

5,6-Sulphinyl-D- or L-gulono-γ-lactone,
5,6-sulphinyl-D- or L-mannono-γ-lactone,
2,3-sulphinyl-L-gulono-γ-lactone,
2,3-sulphinyl-L-mannono-γ-lactone.

The two epi-forms of compounds of formula I, with respect to the 4-position, are also within the scope of the present invention.

The invention is also concerned with a process for the manufacture of compounds of formula I.

This process comprises sulphinylating L-gulonic acid γ-lactone or the corresponding stereoisomer with respect to position 4 or 5, that is D-gulonic acid - or L-mannonic acid - and, respectively, D-mannonic acid γ-lactone.

Finally, the invention is concerned with the use of the compounds of formula I as antioxidants and with compositions having oxidation-inhibiting properties, which contain a compound of formula I.

The sulphinylation of L-gulonic acid γ-lactone or of its stereoisomers is preferably carried out using thionyl chloride as the sulphinylating agent. The reaction partners are conveniently reacted in approximately equimolar amounts, preferably in amounts which are as equimolar as possible. Moreover, the sulphinylation is conveniently carried out at temperatures of about −20° C. to about 50° C. A preferred temperature range is that of about 0° C. to about 30° C.

The reaction is conveniently carried out in the presence of an inert solvent, especially a polar, aprotic solvent. Examples of such solvents are acyclic di- and polyethers such as monoglyme (1,2-dimethoxyethane) and diethylene glycol dimethyl ether; cyclic mono-and diethers such as tetrahydrofuran and dioxan; sulpholane (tetrahydrothiophene 1,1-dioxide); dimethylformamide; dimethylacetamide; N-methylpyrrolidone; and acetonitrile, and the like.

The novel compounds have interesting oxidation-inhibiting properties and can be used in a wide range of substrates, for example:
in foodstuffs [wine (especially for its sulphurization), vinegar, cooking oils and fats, beer, fruit and vegetable juices, syrup, meat and sausage products, dried fruits, dried vegetables, nuts, fruit and vegetable preserves, potato products, spreads, sauces, mayonnaise, etc.]
in feedstuffs
in water used for cooking
in agents for the manufacture and development of films
in printing media
in agents for the manufacture and treatment of textiles
in plastics
in lubricating oils and greases
in rubber.

The amount of the compounds of formula I which can conveniently be used can be kept small in each case; it preferably corresponds to approximately the amount of other antioxidants of the sulphite type which are used, for example conveniently about 1–700 ppm, especially about 20 to about 2000 ppm. The preferred amount depends on the purpose of use. In the foodstuff industry this preferred amount is, for example:

| for wine: | about 50–300 ppm |
| for dried fruit: | about 1000–7000 ppm |
| for fruit and vegetable juices: | about 80–300 ppm |

The novel compounds of formula I can be added as such to the substrate to protected, although they can also be used in diluted form, for example as a solution, especially as an aqueous solution or as an alcoholic solution.

At higher concentrations ($\geq 2$ mg/ml substrate) the compounds of formula I have, moreover, bacteriological and fungicidal activity.

EXAMPLE 178.1 g of L-gulonic acid γ-lactone (1.0 mol) and 400 ml of glass beadlets (diameter =3 mm) in 1000 ml of tetrahydrofuran were placed under a protective gas atmosphere in a 2 l four-necked sulphonation flask having a thermometer, dropping funnel and plate stirrer and cooled to about 0° C. in an ice bath while stirring. 72.6 ml of thionyl chloride (1.0mol) were added thereto and the suspension was stirred vigorously (600 rpm) at 0° C. for 1 hour. The cooling bath was removed and the mixture was stirred at room temperature for 15 hours. The glass beadlets were separated over a slotted glass suction filter without a filter and rinsed with THF. The suspension was poured into a mixture of 500 g of ice, 300 g of water and 1000 ml of ethyl acetate. 162 g of sodium bicarbonate (1.93 mol) were added portionwise while stirring in order to neutralize the hydrochloric acid. The pH value was adjusted to pH =5 by the addition of further sodium bicarbonate. The product was extracted in 4 separating funnels with 4 ×500 ml of ethyl acetate. The organic phases were washed with 3 ×100 ml of water, combined and dried over 250 g of sodium sulphate for 1 hour. The sodium sulphate was filtered off and the filtrate was concentrated in a 2 l round flask on a rotary evaporator (bath temperature =50° C. in a water-jet vacuum. The residue was dissolved in 500 ml of acetone. 550 ml of ethyl acetate were added thereto, the acetone was distilled off on a rotary evaporator under a vacuum and thereafter the residue was crystallized at 0° C. for 18 hours. The product was filtered off under suction and rinsed with 50 ml of ice-cold ethyl acetate. The filter cake was dried to constant weight for 5 hours at 50° C. in a water-jet vacuum. There were obtained 9.5 g of 5,6-sulphinyl-L-gulono-γ-lactone (41% of theory), m.p. 134.7° C., $[\alpha]_{436}^{20}=$ (1% in H$_2$O)$=+197°$.

Because the 5,6-[R/S]-sulphinyl-L-gulono-γ-lactone product was a mixture of the two diastereomeric sulphites (R:S =about 1:1), the melting point and rotation vary according to the content of the two diastereomers.

2,3-Sulphinyl-L-gulono-γ-lactone can be obtained from the mother liquor.

The remaining isomers contemplated hereunder can be obtained in an analogous manner.

We claim:

1. A compound of the formula

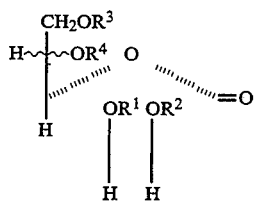

wherein $R^1$ and $R^2$ together represent the —S(O)— group and $R^3$ and $R^4$ represent hydrogen, or $R^3$ and $R^4$ together represent the —S(O)— group and $R^1$ and $R^2$ represent hydrogen, its epimers, racemates, diastereomers, and stereoisomers.

2. The compounds of claim 1 selected from the group consisting of 5,6-Sulphinyl-L-gulono-γ-lactone, 5,6-sulphinyl-D-gulono-γlactone, 5,6-sulphinyl-L-mannono-γ-lactone or 5,6-sulphinyl-D-mannono-γlactone.

3. The compound of claim 1, 2,3-Sulphinyl-L-gulono-γ-lactone.

4. The compound of claim 2, 5,6-sulphinyl-L-gulono-γ-lactone.

5. A process for the manufacture of the compounds of the formula

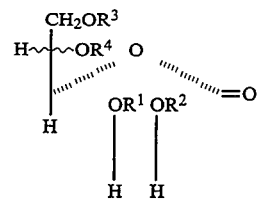

wherein $R^1$ and $R^2$ together represent the —S(O)— group and $R^3$ and $R^4$ represent hydrogen, or $R^3$ and $R^4$ together represent the —S(O)— group and $R^1$ and $R^2$ represent hydrogen, which process comprises sulphinylating L-gulono-γ-lactone or a corresponding stereoisomer.

6. The process according to claim 5, wherein L-gulono-γ-lactone is sulphinylated to 5,6-sulphinyl-L-gulono-γ-lactone.

7. The process according to claim 6, wherein the sulphinylation is carried out using thionyl chloride.

8. A composition having oxidation-inhibiting properties, containing a compound of the formula

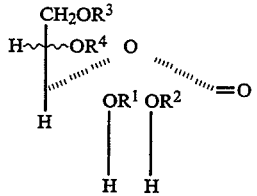

wherein $R^1$ and $R^2$ together represent the —S(O)— group and $R^3$ and $R^4$ represent hydrogen, or $R^3$ and $R^4$ together represent the —S(O)— group and $R^1$ and $R^2$ represent hydrogen, or a stereoisomer thereof.

9. The composition according to claim 8, which contains the compound of formula I, 5,6-sulphinyl-L-gulono-γ-lactone.

* * * * *